United States Patent [19]

Kunii et al.

[11] 4,215,585
[45] Aug. 5, 1980

[54] ULTRASONIC SCANNER

[75] Inventors: Yutaka Kunii; Toshikuni Shimoji; Masaharu Jingu, all of Kawasaki, Japan

[73] Assignee: Tokyo Shibaura Electric Co., Ltd., Japan

[21] Appl. No.: 789,742

[22] Filed: Apr. 21, 1977

[30] Foreign Application Priority Data

Apr. 23, 1976 [JP] Japan .................................. 51/46153

[51] Int. Cl.$^2$ ............................................... A61B 5/00
[52] U.S. Cl. ...................................... 73/633; 128/660; 74/25; 74/116
[58] Field of Search ............... 128/2 V, 2.05 Z, 24 A, 128/660–663; 73/632–633, 618–621, 640, 67.8 S, 71.5 US; 74/22 R, 23, 25, 118, 70, 50, 118

[56] References Cited

U.S. PATENT DOCUMENTS

| | | | |
|---|---|---|---|
| 2,858,711 | 11/1958 | Blackstone et al. | 74/50 |
| 3,060,755 | 10/1962 | De Brosse et al. | 74/22 |
| 3,308,652 | 3/1967 | Appel et al. | 73/621 |
| 3,406,564 | 10/1968 | Phillips et al. | 73/621 |
| 3,741,004 | 6/1973 | Posakony | 73/620 |
| 3,974,826 | 8/1976 | Eggleton et al. | 128/2 V |
| 4,120,291 | 10/1978 | Paton et al. | 128/2 V |

FOREIGN PATENT DOCUMENTS 1112628  5/1968  United Kingdom .................... 128/2 V

OTHER PUBLICATIONS

Griffith et al., "A Sector-Scanner For Real-Time Two-D Echocardiography," Circulation vol. XLIX, Jun. 1974, pp. 1147–1152.
McDicken et al., "A UTS Instrument for Rapid B-Scanning of the Heart", Ultrasonics, vol. 12, #6, Nov. 1974, pp. 269–271.

Primary Examiner—William E. Kamm
Assistant Examiner—Francis J. Jaworski
Attorney, Agent, or Firm—Finnegan, Henderson, Farabow, Garrett & Dunner

[57] ABSTRACT

An ultrasonic scanner, comprising a holder for supporting the ultrasonic probe, said holder being rotatably pivoted by a pivoting shaft, a rotating shaft whose axis is perpendicular to the axis of the pivoting shaft pivoting the holder, and a motion-converting mechanism for converting the rotation of the rotating shaft to a rotatingly reciprocating motion of the ultrasonic probe holder. The ultrasonic scanner can be made small in size, is capable of freely adjusting the rotatingly reciprocating motion, i.e. the head-shaking motion of the ultrasonic probe, and permits readily detecting the rotation angle of the rotating shaft. In addition, the scanner can be housed satisfactorily in a sealed vessel filled with a transmission medium of the ultrasonic beam.

8 Claims, 8 Drawing Figures

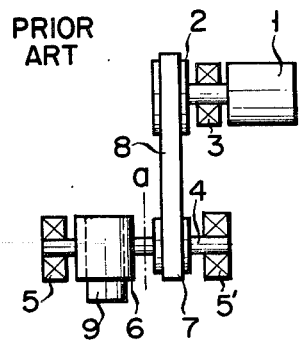
FIG. 1 PRIOR ART
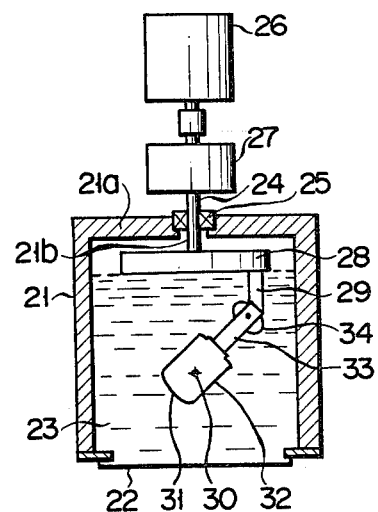
FIG. 2
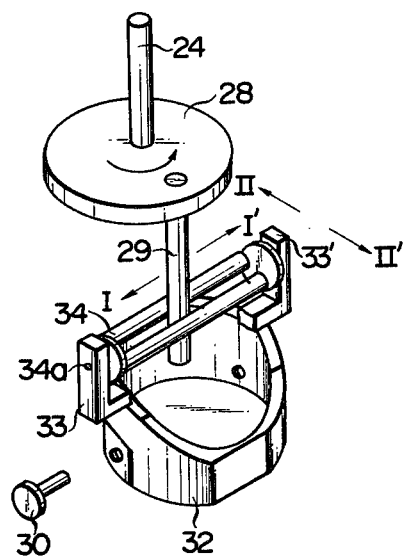
FIG. 3
FIG. 4
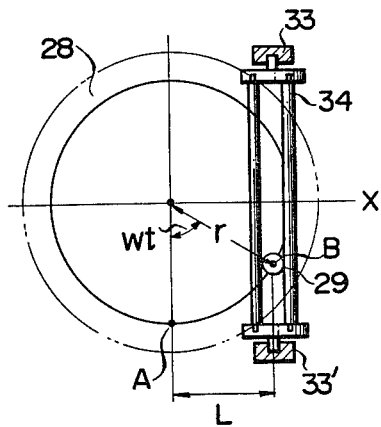
FIG. 5
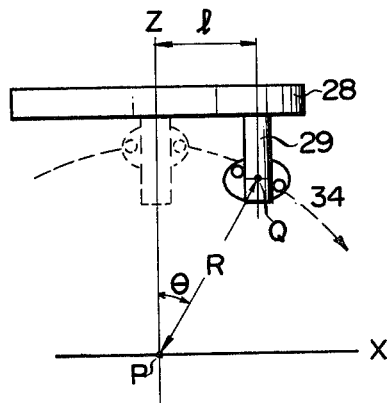

ULTRASONIC SCANNER

BACKGROUND OF THE INVENTION

This invention relates to an ultrasonic scanner used in an ultrasonic diagnostic apparatus.

A tomogram of tissue of a living body can be obtained by irradiating an ultrasonic wave to the tissue. Namely, differences in structure between portions of the tissue lead to differing attenuation of the ultrasonic wave. Thus, the tomogram may be obtained by utilizing the echo of the irradiated ultrasonic wave. Ultrasonic diagnostic apparatuses based on this principle have been developed and applied to various medical fields.

Where an ultrasonic diagnostic apparatus is used for obtaining a tomogram of the heart, a proximity method is employed in general so as to prevent the influences of the ribs. The proximity method is a technique where an ultrasonic probe is settled as close as possible to the surface of the body under examination so as to enable the ultrasonic beam to be scanned through the space between two adjacent ribs.

The ultrasonic beam can be scanned in two ways; linear scan and sector scan. The sector scan is directed to the manner of scanning the ultrasonic beam by shaking the ultrasonic probe in a sector form. When it is intended to obtain a tomogram of the heart by the promixity method which necessitates scanning the beam through a very small space between two adjacent ribs, the sector scan is very effective.

Appended FIG. 1 shows a conventional ultrasonic high speed scanner performing sector scan, which is disclosed in the U.S. Pat. No. 3,927,661. As shown in the drawing, a pulley 2 is fixed to the shaft of a motor 1, said shaft being supported by a bearing 3. Further, an ultrasonic probe holder 6 and a pulley 7 are fixed to a transmission shaft 4 supported by bearings 5 and 5' and a transmission belt 8 is stretched between the pulleys 2 and 7. Still further, an ultrasonic probe 9 emitting and receiving an ultrasonic beam is mounted to the probe holder 6. The motor 1 is driven in clockwise and counterclockwise directions alternately and this particular rotation of the motor is transmitted to the transmission shaft 4 via the transmission belt 8 and the pulleys 2,7. Accordingly, the ultrasonic probe 9 fixed to the transmission shaft 4 is allowed to perform the sector scan.

The device of FIG. 1, however, is not satisfactory in that the ultrasonic probe fails to perform the sector scan at a high speed. In addition, the motor must provide a large torque, thereby rendering the entire device bulky. It should be noted in this connection that the ultrasonic scanner must be light and small because the scanner is hand held for operation particularly where the proximity method is applied for the diagnosis of the heart.

Also known is an ultrasonic scanner in which the rotation of the motor is converted to a rotatingly reciprocating motion, i.e., a head-shaking motion, of the ultrasonic probe by using a link mechanism. The scanner of this type, however, is defective in that the head-shaking motion lacks smoothness, rendering it difficult to enlarge the head-shaking angle of the probe, and that it is difficult to detect the scanning angle of the beam in spite of the fact that the angle detection is necessary for obtaining the image of the reflected beam.

As described previously, the ultrasonic diagnosis makes it necessary in general to settle the ultrasonic probe as close as possible to the surface of the body under examination. To achieve this, there is an effective technique referred to as the immersion method, namely, the ultrasonic probe is immersed in a transmission medium of the ultrasonic beam such as water, castor oil or liquid paraffin housed in a vessel. The vessel filled with the liquid mentioned is disposed in contact with the surface of the body under examination so as to enable the ultrasonic beam to be transmitted and received through the liquid-filled vessel. In this case, the vessel itself must be hand held in operating the ultrasonic scanner. Thus, it is customary in this immersion method to seal the vessel so as to prevent the liquid acting as the ultrasonic beam transmitting medium from spilling therefrom. Attention should be paid here to the aspect that the ultrasonic probe should perform the head-shaking motion within the vessel filled with the transmission medium of the ultrasonic beam. Naturally, it is necessary to reduce the power consumption of the apparatus in order to minimize the size of the apparatus. For example, the apparatus of FIG. 1 should be constructed such that the right hand portion divided by the dotted line a is disposed outside of the vessel. When it comes to the apparatus equipped with a link mechanism, it is necessary to dispose the link mechanism outside of the vessel. A major problem involved in these structures is that the rotatingly reciprocating motion generated outside of the vessel should be transmitted to the ultrasonic probe disposed within the vessel. Needless to say, it is quite difficult to seal the vessel in a manner to permit the transmission of the rotatingly reciprocating motion.

SUMMARY OF THE INVENTION

An object of this invention is to provide an ultrasonic scanner small in size, capable of freely adjusting the head-shaking angle of an ultrasonic probe, permitting an easy detection of the head-shaking angle of the probe, and enabled to be housed in a sealed vessel. The ultrasonic scanner according to this invention comprises a holder for holding an ultrasonic probe, pivoting shaft for rotatably pivoting the probe holder, a rotating shaft whose axis is perpendicular to the axis of the pivoting shaft pivoting the probe holder, and a mechanism for converting the rotary motion of the rotating shaft to a rotatingly reciprocating motion of the ultrasonic probe holder.

BRIEF DESCRIPTION OF THE DRAWINGS

FIG. 1 schematically shows a conventional ultrasonic scanner,

FIG. 2 is a cross sectional view showing the state in which an ultrasonic scanner according to one embodiment of this invention is housed in a vessel filled with a liquid substance, FIG. 3 is an oblique view showing the motion-converting mechanism of the ultrasonic scanner shown in FIG. 2, FIGS. 4 and 5 are intended to explain the principle of detecting the inclination angle of the ultrasonic probe mounted to the ultrasonic scanner of FIG. 2 and FIGS. 6 to 8 are oblique views showing modifications of the ultrasonic scanner according to this invention.

DETAILED DESCRIPTION OF THE PREFERRED EMBODIMENT

Figure 6:
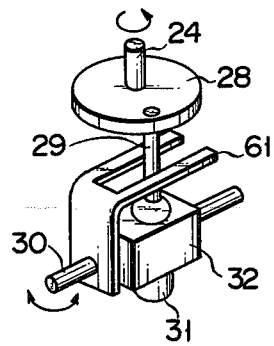

As shown in FIG. 2, it is convenient to employ the immersion method in embodying this invention. It is seen in the drawing that the bottom opening of a vessel 21 is sealed with a membrane 22 made of a material which transmits an ultrasonic beam. The vessel 21 is filled with a liquid substance acting as the ultrasonic beam transmission medium 23.

A hole 21b is bored through an upper wall 21a of the vessel 21. Naturally, the hole 21b is positioned at the center of the upper wall 21a. It is seen that a rotating shaft 24 supported by a bearing 25 penetrates through the hole 21b. One end of the rotating shaft 24, which is disposed outside of the vessel 21, is fixed to a motor 26 via a detector 27 for detecting the rotation angle of the shaft 24.

A rotary disc 28, which is not necessarily circular, is fixed to the other end of the rotating shaft 24. Near the periphery of the disc 28, there is provided a transmission rod 29 extending vertically downward from the disc.

An ultrasonic probe 31 is supported by a cylindrical holder 32 which is rotatably pivoted by pivoting shaft 30. It is important to note that the axis of the pivoting shaft 30 is perpendicular to the axis of the rotating shaft 24. Further, the holder 32 and consequently the probe 31 make head-shaking motions around the axis of the pivoting shaft 30.

A pair of support members 33 and 33' are mounted to the upper end of the holder 32, and a guide member 34 provided by two bars arranged in parallel with the axis of the pivoting shaft 30 is mounted between the support members 33 and 33'. The ends of the guide member 34 are fixed to plates which are rendered rotatable around the common axis 34a of the plates. As best shown in FIG. 3 of the drawing, the lower portion of the transmission rod 29 fixed to the rotary disc 28 extends downward through the clearance between the two bars constituting the guide member 34.

The ultrasonic scanner constructed as described above performs the following function. When the motor 26 is rotated in one direction, the rotary disc 28 fixed to the motor 26 via the rotating shaft 24 is also rotated in the same direction. In this case, the transmission rod 29 fixed to the disc 28 is allowed to draw a circular locus about the axis of the rotating shaft 24.

What is particularly important in the apparatus described is that the rod 29 extends through the clearance between the two bars of the guide member 34 and that the ultrasonic probe holder 32 is rotatably pivoted by the pivoting shaft 30. Specifically, rotation of the rotary disc 28 causes the transmission rod 29 to make a reciprocating motion within the clearance between the two bars of the guide member 34 in an I—I' direction as shown in FIG. 3. In this case, motion of the rod 29 causes the guide member 34 to make a reciprocating motion in an II—II' direction as shown in FIG. 3. It is of no difficulty to understand the particular function of the transmission rod 29 when it is taken into account that the rod 29 makes a circular motion around the axis of the rotating shaft 24.

As described above, the holder 32 is rotatably pivoted by the pivoting shaft 30. It follows that the reciprocating motion of the guide member 34 in the II—II' direction causes the ultrasonic probe 31 supported by the holder 32 to make a reciprocating motion, i.e., head-shaking motion, about the axis of the pivoting shaft 30. In other words, rotation of the motor 26 is converted to the head-shaking motion of the ultrasonic probe 31.

The motion-converting mechanism comprising the rotary disc 28, the transmission rod 29 and the guide member 34 can be made very small in size and housed in the vessel 21 as shown in FIG. 2. An important feature to be noted here is that the motion-converting mechanism housed in the vessel 21 is connected to the motor 26 disposed outside of the vessel 21 by the rotating shaft 24 alone extending through the hole 21b of the vessel. Naturally, the vessel 21 can be sealed without difficulty. Incidentally, it is very difficult to seal a vessel in a conventional system in which the reciprocating motion made outside of the vessel is transmitted to the mechanism housed in the vessel.

An additional feature to be noted is that the ultrasonic probe 31 is allowed to make a head-shaking motion by the reciprocating force given to one extreme end of the ultrasonic probe holder 32 which is supported by the pivoting shaft 30. In contrast, the conventional apparatus such as the one shown in FIG. 1 is constructed such that the ultrasonic probe, or the holder supporting the probe, is fixed to the rotating shaft. Namely, the probe is allowed to make a head-shaking motion by the rotary force of the shaft. Clearly, the construction of this invention is advantageous in that the ultrasonic probe holder 32 alone is fitted to the pivoting shaft 30, rendering it markedly convenient to house the probe 31 in the vessel 21.

It should also be noted that the motor 26 and, thus, the rotating shaft 24 of this invention rotate in one direction, rendering it easy to detect the rotating angle of the shaft 24. The head-shaking angle of the ultrasonic probe can be readily calculated on the basis of the rotating angle of the shaft 24 thus detected as explained in the following with reference to FIGS. 4 and 5.

If the rotary disc 28 rotates in a counterclockwise direction in this case, the center B of the transmission rod 29 fixed to the disc 28 moves from the point A to the position making an angle $\omega t$ as shown in FIG. 4 "t" seconds after the start of the rotation of the disc 28. Naturally, the mark "$\omega$" denotes the angular speed of the disc rotation. At this time, the intersection Q of the axis of the transmission rod 29 and the line joining the centers of the two bars of the guide member 34 is positioned in a point making an angle $\theta$ with the intersection P of the Z-axis of the XZ coordinates and the axis of the pivoting shaft 30 as shown in FIG. 5. In the co-ordinates mentioned, the Z-axis represents the axis of the rotating shaft 24, with the X-axis denoting the line perpendicular to with the Z-axis and the axis of the pivoting shaft 30 from point P.

Referring to FIG. 4, the radial distance of the center B of the rod 29 from the center of the rotary disc 28 is set at "r". It follows that the displacement L of the center B in the X-direction during the period of time "t" is as follows:

$$L = r \sin \omega t \tag{1}$$

Likewise, the displacement l (FIG. 5) of the intersection Q in the X-direction during the period of time "t" can be represented by the following equation (2):

$$l = R \sin \theta \tag{2}$$

Needless to say, "R" in equation (2) denotes the length of the line between points P and Q.

Clearly, "L" in equation (1) is equal to "l" in equation (2). Thus:

$$r \sin \omega t = R \sin \theta \tag{3}$$

The following equation (4) can be derived from the equation (3):

$$\theta = \sin^{-1}(r/R \sin \omega t) \quad (4)$$

Equation (4) shows that the angle $\theta$, i.e., the inclination of the ultrasonic probe 31, can be readily calculated on the basis of the detected value $\omega t$.

As described in detail, the ultrasonic scanner of this invention permits detecting the head-shaking angle of the ultrasonic probe at a high accuracy. Further, the head-shaking angle can readily be adjusted by adjusting the radial distance of the transmission rod 29 from the center of the rotary disc 28.

In the embodiment described, the axis of the pivoting shaft 30 rotatably pivoting the ultrasonic probe holder is perpendicular to the rotating shaft 24. However, the axis may be made parallel with the axis of the rotating shaft, with a satisfactory result. It this case, the plane including the upper or lower surface of the rotary disc is naturally rendered perpendicular to the common axis mentioned. Likewise, the guide member 34 consisting of two bars is mounted to extend in a direction perpendicular to the axis of the pivoting shaft rotatably pivoting the holder 32. As in the previous case, the transmission rod 29 fixed to the rotary disc 28 is allowed to slide within the clearance between the two bars of the guide member 34.

In this arrangement, there is provided a U-shaped guide member which is connected to the guide member 34 by a transmission shaft. This transmission shaft extends in a direction perpendicular to the length of the guide member 34. Also provided is a rod leading to the upper end of the ultrasonic probe holder 32. This rod is perpendicular to the transmission shaft under the rest state of the apparatus. During the operation of the apparatus, the upper portion of the rod mentioned is allowed to slide within the groove of the U-shaped guide member.

In the mechanism of this construction, circular motion of the transmission rod 29 fixed to the rotary disc 28 causes the guide member 34 and the transmission shaft to make a linear reciprocating motion in a direction perpendicular to the axis of the pivoting shaft pivoting the ultrasonic probe holder. Thus, the rod leading to the upper end of the holder 32 makes a head-shaking motion about the axis of the pivoting shaft 30 rotatably pivoting the holder 32, while making a sliding motion within the groove of the U-shaped guide member.

Figure 7:
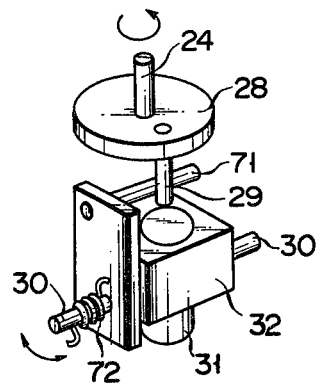
Figure 8:
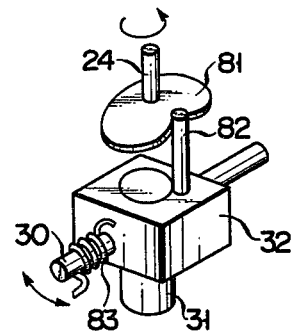

FIGS. 6 to 8 show modifications of the scanner according to this invention. In the apparatus of FIG. 6, a guide member 61 is shaped to form a letter "U". The apparatus of this type performs the function equivalent to that performed by the apparatus shown in FIGS. 2 and 3.

In FIG. 7, a single guide bar 71 is used and a coil spring 72 is wound round the shaft 30 pivoting the ultrasonic probe holder 32. The coil spring 72 exerts a bias force in one direction all the time on the ultrasonic probe holder 32, thereby keeping the guide bar 71 in contact with the transmission rod 29 fixed to the rotary disc 28. Accordingly, circular motion of the rod 29 causes the guide bar 71 to perform a rotatingly reciprocating motion, resulting in the ultrasonic probe holder 32 making a head-shaking motion about the axis of the shaft 30.

In the apparatus of FIG. 7, it is possible to reduce the required torque of the motor by appropriately selecting the coil spring used. Specifically, the system comprising the ultrasonic probe 31, the holder 32, and the guide bar 71 may be regarded as a vibration system. Thus, it is possible to select the spring 72 of a spring constant enabling the vibration system to resonate with the angular speed $\omega$ of the motor. In this case, the torque of the motor can naturally be reduced. An additional merit to be noted is that the head-shaking angle of the ultrasonic probe is brought into zero by the bias force of the spring when the motor has been disconnected from the power source, in which the torque of the motor is reduced to zero.

In the apparatus of FIG. 8, a cam 81, not a disc, is fixed to the rotating shaft 24. Further, a guide bar 82 is fixed to the ultrasonic probe holder 32 in a manner to make a contact with the outer periphery of the cam 81. In this case, the bias force of a coil spring wound round the pin 30 serves to keep the guide bar 82 in contact with the outer periphery of the cam 81.

The apparatus of FIG. 8 is advantageous in that the head-shaking motion of the ultrasonic probe is enabled to be uniform in angular speed. A uniform angular speed is important in permitting a uniform density of the ultrasonic beam. Incidentally, the ultrasonic probe of each of the apparatus shown in FIGS. 2 to 7 fails to perform a head-shaking motion at a uniform angular speed when the motor rotates at a uniform angular speed. However, the ultrasonic probe of the apparatus shown in FIG. 8 is enabled to perform a head-shaking motion at a uniform angular speed by appropriate selection of the cam shape. A cam permitting a uniform angular speed is provided, for example by, a partially recessed circular body.

As described in detail, the ultrasonic scanner according to this invention is simple in structure, small in size, capable of readily detecting the head-shaking angle of the ultrasonic probe at a high accuracy, and presents no difficulty in operation. In addition, the head-shaking angle of the ultrasonic probe can be adjusted without difficulty.

What we claim is:

1. An ultrasonic scanner for rotatably reciprocating an ultrasonic probe to sector scan a subject to be examined comprising:
    a pivotable holder for supporting the ultrasonic probe;
    a pivoting shaft pivotably mounted on said holder for permitting the holder to be reciprocated rotatably about the pivoting shaft;
    a rotatable drive shaft having an axis perpendicular to the axis of the pivoting shaft; and
    transmission means for transforming the rotary motion of the drive shaft to a rotatably reciprocating motion of the ultrasonic probe, said means including:
    (i) a guide member provided at one end of the holder and having a longitudinal slide means which remains parallel to the axis of the pivoting shaft throughout the rotatable reciprocation of the holder about the pivoting shaft;
    (ii) a rotary member fixedly coupled to the drive shaft; and
    (iii) a transmission rod parallel to said drive shaft, said transmission rod having one end connected to the rotary member at a predetermined distance from the axis of the drive shaft and the other end slideably engaged with said longitudinal slide means to impart through said guide member, upon the rotation of the drive shaft and rotary member, a rotably reciprocating motion to the holder and the ultrasonic probe about the axis of the pivoting shaft, and wherein the inclination angle $\theta$ defined between the axis of the ultrasonic probe and that of the drive shaft is represented by:

$$\theta = \sin^{-1}(r/R \sin wt)$$

where
- r: radial distance of the axis of the transmission rod from the axis of the drive shaft,
- R: radial distance between the intersection of the axis of the drive shaft with the axis of the pivoting shaft and the intersection of the axis of the transmission rod with the longitudinal slide means of the guide member,
- w: angular speed of the transmission rod about the axis of the drive shaft, and
- t: rotating time of the rotary member from a resting position at which t=0 and said inclination angle ($\theta$)=0.

2. The ultrasonic scanner according to claim 1, wherein the guide member is provided by two rods arranged in parallel with the axis of the pivoting shaft, the ends of the two rods being fixed to a pair of plates each rotatably mounted to one end of the holder, and the lower portion of the transmission rod fixed to the rotary member being slidable within the clearance formed between the two rods constituting the guide member.

3. The ultrasonic scanner according to claim 1, wherein the guide member comprises two arms extending in parallel with the axis of the pivoting shaft and a bar joining these two arms in a manner to form a letter "U", and the lower portion of the transmission rod fixed to the rotary member is slidable within the clearance between the two arms.

4. The ultrasonic scanner according to claim 1, wherein the guide member is provided by a single rod and the pivoting shaft for pivoting the holder is wound with a coil spring, the coil spring imparting a continuous bias force in one direction to the ultrasonic probe holder so as to keep the guide member in contact with the transmission rod fixed to the rotary member.

5. Ultrasonic scanner according to claim 1 wherein said rotary member is a rotary disk and wherein the scanner further comprises a pair of support members for supporting said guide member so as to be rotatably pivoted at both ends.

6. An ultrasonic scanner comprising:
an ultrasonic probe;
a holder for supporting the ultrasonic probe;
a pivoting shaft for pivoting the holder;
a power-driven rotating shaft whose axis is perpendicular to the axis of the pivoting shaft; and
transmission means for transforming the rotary driving power from the rotating shaft to a rotatably reciprocating motion of the ultrasonic probe, said means including:
  (i) a guide member provided at one end of the holder and having an axis extending in parallel with the axis of the pivoting shaft;
  (ii) a rotary member coupled to the rotating shaft; and
  (iii) a transmission rod havine one end connected to the rotary member at a predetermined distance from the axis of the rotating shaft and the other end slidably engaged with the guide member wherein the transmission rod has circular motion about the axis of the rotating shaft upon rotation of the rotary member and reciprocating motion along the axis of the guide member, and wherein the motion of the transmission rod imparts through said guide member a rotatably reciprocating motion to the holder and ultrasonic probe about the axis of the pivoting shaft, and wherein the inclination ($\theta$) defined between the axis of the ultrasonic probe and that of the rotating shaft is represented by:

$$\theta = \sin^{-1}(r/R \sin \omega t)$$

where
- r: radial distance of the axis of the transmission rod from the axis of the rotating shaft,
- R: radial distance between the intersection of the axis of the rotating shaft with the axis of the pivoting shaft and the intersection of the axis of the transmission rod with the axis of the guide member,
- $\omega$: angular speed of the transmission rod about the axis of the rotating shaft, and
- t: rotating time of the rotary member.

7. An ultrasonic scanner for rotatably reciprocating an ultrasonic probe to sector scan a subject to be examined comprising:
a pivotable holder for supporting the ultrasonic probe;
a pivoting shaft pivotably mounted on said holder for permitting the holder to be reciprocated rotatably about the pivoting shaft,
a rotatable drive shaft having an axis perpendicular to the axis of the pivoting shaft, and
transmission means for transforming the rotary motion of the drive shaft to a rotatably reciprocating motion of the ultrasonic probe about the pivot shaft, said means including:
  (i) a guide member including two rods arranged in parallel with the axis of the pivoting shaft, the ends of the two rods being fixed to a pair of plates each rotatably mounted to one end of the holder,
  (ii) a rotary member fixedly coupled to the drive shaft, and
  (iii) a transmission rod parallel to said drive shaft, said transmission rod having one end connected to the rotary member at a predetermined distance from the axis of the drive shaft and the other end slidably engaged within the clearance formed between the two rods of the guide member to impart through said guide member, upon the rotation of the drive shaft and rotary member, a rotatably reciprocating motion to the holder and the ultrasonic probe about the axis of the pivoting shaft.

8. An ultrasonic scanner for rotatably reciprocating an ultrasonic probe to sector scan a subject to be examined comprising:
a pivotable holder for supporting the ultrasonic probe;
a pivoting shaft pivotably mounted on said holder for permitting the holder to be reciprocated rotatably about the pivoting shaft, a rotatable drive shaft having an axis perpendicular to the axis of the pivoting shaft, and transmission means for transforming the rotary motion of the drive shaft to a rotatably reciprocating motion of the ultrasonic probe about the pivot shaft, said means including:
(i) a rotary member fixedly coupled to the drive shaft,
(ii) a transmission rod parallel to said drive shaft, said transmission rod having one end connected to the rotary member at a predetermined distance from the axis of the drive shaft, and
(iii) a guide member including a single rod extending parallel to the axis of the pivoting shaft and a coil spring wound about the pivoting shaft for imparting a continuous bias force to keep the guide member in contact with the transmission rod, the end of said transmission rod opposite said rotary member being slidably engaged with said single rod of the guide member to impart through said guide member, upon the rotation of the drive shaft and rotary member, a rotatably reciprocating motion to the holder and the ultrasonic probe about the axis of the pivoting shaft.

* * * * *